United States Patent
Inoue et al.

(10) Patent No.: US 9,557,277 B2
(45) Date of Patent: Jan. 31, 2017

(54) INSPECTION APPARATUS AND INSPECTION METHOD

(71) Applicant: NuFlare Technology, Inc., Yokohama (JP)

(72) Inventors: Hiromu Inoue, Kanagawa (JP); Riki Ogawa, Kanagawa (JP)

(73) Assignee: NuFlare Technology, Inc., Yokohama (JP)

( * ) Notice: Subject to any disclaimer, the term of this patent is extended or adjusted under 35 U.S.C. 154(b) by 420 days.

(21) Appl. No.: 14/059,847

(22) Filed: Oct. 22, 2013

(65) Prior Publication Data

US 2014/0111636 A1    Apr. 24, 2014

(30) Foreign Application Priority Data

Oct. 23, 2012 (JP) .................................. 2012-234122

(51) Int. Cl.
  *G01N 21/00* (2006.01)
  *G01N 21/956* (2006.01)

(52) U.S. Cl.
  CPC ...... *G01N 21/956* (2013.01); *G01N 21/95607* (2013.01)

(58) Field of Classification Search
  CPC ...... G01N 21/00; G01N 2201/00; G01B 11/00
  USPC .......................................... 356/237.2–237.6
  See application file for complete search history.

(56) References Cited

U.S. PATENT DOCUMENTS

| | | | | |
|---|---|---|---|---|
| 5,530,237 A | * | 6/1996 | Sato | G02B 21/245 250/201.4 |
| 6,798,493 B2 | * | 9/2004 | Imanishi | B82Y 10/00 355/55 |
| 6,900,888 B2 | * | 5/2005 | Yoshida | G03F 7/7065 250/559.4 |

(Continued)

FOREIGN PATENT DOCUMENTS

JP  03-050513 A  3/1991
JP  06-109660 A  4/1994

(Continued)

OTHER PUBLICATIONS

U.S. Appl. No. 14/153,199, filed Jan. 13, 2014, Ogawa, et al.

(Continued)

*Primary Examiner* — Tarifur Chowdhury
*Assistant Examiner* — Isiaka Akanbi
(74) *Attorney, Agent, or Firm* — Oblon, McClelland, Maier & Neustadt, L.L.P.

(57) ABSTRACT

An inspection apparatus comprising, a focal position detector that detects a reference focal position of an image plane of a sample from a variation of an output value in optical image data of the sample, the output value being acquired by changing a distance between a first lens and the sample, and detects an optimum focal position of an inspection from the reference focal position, an image processor that obtains at least one of either an average gradation value in each predetermined unit region or a variation of a gradation value in the unit region with respect to the optical image data obtained at the optimum focal position, and a defect detector that detects a defect of the sample based on at least one of either the average gradation value or the variation of the gradation value.

9 Claims, 11 Drawing Sheets

(56) References Cited

U.S. PATENT DOCUMENTS

| | | | | |
|---|---|---|---|---|
| 2004/0070753 A1* | 4/2004 | Sugihara | .......... | G01N 21/95607 356/237.5 |
| 2007/0280664 A1* | 12/2007 | Ikeda | ....................... | G02B 7/08 396/114 |
| 2010/0247085 A1* | 9/2010 | Shiratsuchi | ............ | G03B 13/00 396/104 |
| 2011/0255770 A1* | 10/2011 | Touya | ..................... | G06T 7/001 382/144 |
| 2014/0002826 A1 | 1/2014 | Inoue et al. | | |
| 2014/0240700 A1* | 8/2014 | Ogawa | ................... | G01N 21/01 356/244 |

FOREIGN PATENT DOCUMENTS

| | | |
|---|---|---|
| JP | 08-152550 A | 6/1996 |
| JP | 2000-009655 A | 1/2000 |
| JP | 2003-125411 | 4/2003 |
| JP | 2007-232930 | 9/2007 |
| JP | 2008-134214 A | 6/2008 |
| JP | 4236825 | 12/2008 |
| WO | WO 2007/043535 | 4/2007 |

OTHER PUBLICATIONS

U.S. Appl. No. 14/185,333, filed Feb. 20, 2014, Ogawa, et al.
Japanese Office Action issued in Japanese Patent Application No. 2012-234122 (with English translation), 6 pages.

\* cited by examiner

INSPECTION APPARATUS AND INSPECTION METHOD

CROSS-REFERENCE TO THE RELATED APPLICATION

The entire disclosure of the Japanese Patent Application No. 2012-234122, filed on Oct. 23, 2012 including specification, claims, drawings, and summary, on which the Convention priority of the present application is based, are incorporated herein in its entirety.

FIELD OF THE INVENTION

This invention relates to an Inspection Apparatus and Inspection Method.

BACKGROUND

A circuit dimension required for a semiconductor element becomes finer and finer with high integration and large capacity of a Large Scale Integration (LSI).

Using an original image pattern (referring to a mask or a reticle, hereinafter collectively referred to as a mask) in which a circuit pattern is formed, a circuit is formed by exposing and transferring a pattern onto a wafer with a reduced-projection exposure apparatus that is called a stepper or a scanner, thereby reproducing the semiconductor element.

It is necessary to improve yield in the costly production of the LSI. Furthermore, the state-of-the-art device is brought into a stage where the formation of the pattern having a line width of ten-odd nanometers is required. At this point, a shape defect of a mask pattern is cited as a large factor in contributing to degradation of the yield. Specifically, examples of the shape defect include irregularity (edge roughness) at a pattern edge, a line width abnormality of the pattern, and a gap abnormality with the adjacent pattern due to a position deviation of the pattern.

The shape defect of the mask pattern becomes finer with the finer dimension of an LSI pattern formed on a semiconductor wafer. Because fluctuations of process conditions are absorbed by enhancing dimension accuracy of the mask, it is necessary to defect an extremely small defect of the pattern in a mask inspection. Therefore, high accuracy is required for an apparatus that inspects the pattern of a transfer mask used in the LSI production. Japanese Patent No. 4236825 discloses an inspection apparatus that can detect fine defects on the mask.

Nanoimprint Lithography (NIL) attracts attention as a technology for forming the fine pattern. In the technology, a mold (a die) having a nanoscale fine structure is pressed onto a resist on the wafer with a pressure to form the fine pattern in the resist.

In a nanoimprint technology, in order to improve productivity, a plurality of replicated patterns (hereinafter referred to as daughter patterns) are prepared using a master pattern that constitutes an original plate, and the daughter patterns are used while mounted on different nanoimprint apparatuses. It is necessary that the daughter pattern be produced so as to correspond collectively to the master pattern, and it is necessary to inspect both the master pattern and the daughter pattern with high accuracy in an inspection process.

At this point, generally the mask is formed with the dimension four times the circuit dimension. After the pattern is reduced and exposed on the resist on the wafer with the reduced-projection exposure apparatus using the mask, development is performed to form the semiconductor circuit pattern. However, in the nanoimprint lithography, the master pattern and the daughter pattern are formed with the same dimension as the circuit dimension. For this reason, the shape defects in the master pattern and the daughter pattern have a large influence on the pattern transferred onto the wafer compared with the pattern of the mask. Accordingly, compared with the pattern of the mask, higher accuracy is required for the inspections of the master pattern and the daughter pattern.

In the inspection apparatus, the sample is irradiated with light emitted from a light source through an optical system. The sample is placed on a table, and the sample is scanned with the light by moving the table. An image of the light transmitted through or reflected from the sample is formed on an image sensor via a lens. The defect of the sample is inspected based on optical image data obtained by the image sensor.

However, in the master pattern and the daughter pattern, the pattern dimension is smaller than the resolution of the optical system in the inspection apparatus. Therefore, it is difficult to accurately detect the focal position. For example, in a focal position detection method in which an optical level method is adopted, the sample is irradiated with the light from the light source through an objective lens, and the image of the image of the light reflected from the sample is formed on a position sensor. Therefore, a displacement amount from a focal position is obtained such that contrast reaches the maximum, and control is performed so as to properly obtain a distance between the sample and the objective lens. However, when the line width of the pattern on the sample is less than or equal to a wavelength, the image of diffracted light generated in the pattern is formed on the position sensor, but the displacement amount cannot accurately be obtained.

It is conceivable that the focal position is measured by providing reference planes on four corners in an inspection area of the sample, and that the focal position is adjusted in the inspection area based on the reference planes. However, when pressure or temperature changes in the inspection process, the focal position of the light with which the sample is irradiated fluctuates height data in the reference plane. For example, because a refractive index of air changes when the pressure changes, an imaging plane of an object, namely, the focal position changes. Accordingly, it is difficult for the focal position to always be accurately adjusted by this method.

The present invention has been devised to solve the problems described above, and an object of the present invention is to provide a focal position detection apparatus and a focal position detection method, which can detect the focal position of the sample having a repetitive pattern in which the period is less than or equal to the resolution of the optical system.

Another object of the present invention is to provide an inspection apparatus and an inspection method, which can detect the defect in the repetitive pattern in which the period is less than or equal to the resolution of the optical system.

Other challenges and advantages of the present invention are apparent from the following description.

SUMMARY OF THE INVENTION

According to one aspect of the present invention, an inspection apparatus comprising, a light source that emits light having a predetermined wavelength, a first lens that transmits the light having the predetermined wavelength toward a sample, a second lens that forms an image of the light transmitted through or reflected by the sample via the first lens, an image sensor that obtains optical image data of a pattern formed on the sample from the light of which the image is formed by the second lens, a focal position detector that detects a reference focal position of an image plane of the sample from a variation of an output value in optical image data of the sample, the output value being acquired by changing a distance between the first lens and the sample, and detects an optimum focal position of an inspection from the reference focal position, an image processor that obtains at least one of either an average gradation value in each predetermined unit region or a variation of a gradation value in the unit region with respect to the optical image data obtained at the optimum focal position, and a defect detector that detects a defect of the sample based on at least one of either the average gradation value or the variation of the gradation value, wherein a resolution limit determined by a wavelength of the light source and a numerical aperture of the second lens is a value in which the pattern is not resolved.

Further to this aspect of the present invention, the inspection apparatus, further comprising, a table on which the sample is placed, and a controller that adjusts a level of the table based on the optimum focal position detected by the focal position detector.

Further to this aspect of the present invention, the inspection apparatus, wherein a support member that supports the sample is provided in the table, and the support member is disposed so as to support the sample at three points.

Further to this aspect of the present invention, the inspection apparatus, wherein the output value is a gradation value of the optical image data.

In another aspect of the present invention, an inspection apparatus comprising, a light source that emits light having a predetermined wavelength, a first lens that transmits the light having the predetermined wavelength toward a sample, a second lens that forms an image of the light transmitted through or reflected by the sample via the first lens, a first image sensor that obtains optical image data of a pattern formed on the sample from the light of which the image is formed by the second lens, an optical path splitting unit that is disposed between the second lens and the first image sensor to split the light transmitted through the second lens, a second image sensor that obtains pieces of image information on focal points ahead and behind the pattern from the pieces of light split by the optical path splitting unit, a focal position detector that detects a reference focal position of an image plane of the sample in the first image sensor from a variation of an output value in the pieces of image information on the focal points ahead and behind the pattern, the output value being acquired by changing a distance between the first lens and the sample, and detects an optimum focal position of an inspection from the reference focal position, an image processor that obtains at least one of either an average gradation value in each predetermined unit region or a variation of a gradation value in the unit region with respect to the optical image data obtained at the optimum focal position; and a defect detector that detects a defect of the sample based on at least one of either the average gradation value or the variation of the gradation value, wherein a resolution limit determined by a wavelength of the light source and a numerical aperture of the second lens is a value in which the pattern is not resolved.

Further to this aspect of the present invention, the inspection apparatus, further comprising, a table on which the sample is placed, and a controller that adjusts a level of the table based on the optimum focal position detected by the focal position detector.

Further to this aspect of the present invention, the inspection apparatus, wherein a support member that supports the sample is provided in the table, and the support member is disposed so as to support the sample at three points.

Further to this aspect of the present invention, the inspection apparatus, wherein the output value is a gradation value of the optical image data.

In another aspect of the present invention, an inspection method comprising the steps of, irradiating a sample with light having a predetermined wavelength via a first lens, forming an image of the light transmitted through or reflected by the sample on an image sensor via a second lens, and obtaining optical image data of a pattern by performing an action to obtain the optical image data of the pattern formed in the sample with a distance between the first lens and the sample changed, detecting a reference focal position of an image plane of the sample from a variation of an output value in optical image data, and detecting an optimum focal position of an inspection from the reference focal position, adjusting a level of a table on which the sample is placed based on the optimum focal position, obtaining at least one of either an average gradation value in each predetermined unit region or a variation of a gradation value in the unit region with respect to the optical image data obtained at the optimum focal position, and detecting a defect of the sample based on at least one of either the average gradation value or the variation of the gradation value, wherein the pattern is a repetitive pattern having a period less than or equal to resolution determined by the wavelength and a numerical aperture of the second lens.

Further to this aspect of the present invention, the inspection method, wherein the sample is supported at three points by a support member provided in the table.

Further to this aspect of the present invention, the inspection method, wherein the optimum focal position is a focal position that is deviated from the reference focal position by a predetermined offset amount.

DETAILED DESCRIPTION OF THE EMBODIMENTS

In the case that the image of the dense pattern having the line width of 100 nm or less is formed, even if the lens (a numerical aperture NA of 1) of a theoretical limitation is used, the pattern cannot be resolved with the optical system in which the DUV (Deep Ultraviolet radiation) light is used. Accordingly, it is difficult to detect the distance between the objective lens and the sample when the proper focal position of the optical system with respect to the pattern, namely, the contrast of the pattern reaches the maximum.

Many patterns formed on the wafer are repetitive patterns such as the line and space pattern, namely, the regular patterns having periodic repetition. For example, the repetitive pattern is formed in the master pattern or daughter pattern, which is used in the nanoimprint lithography.

In the repetitive pattern, for example, when the edge roughness is partially increased, when the pattern is partially lacking, or when the line width is partially narrowed, a disturbance is generated in the regularity thus changing an output value of the optical image data. Even the edge roughness, which does not lead to the defect, varies the output value of the optical image data. In a line pattern drawn by an electron beam shot, the fluctuation of the output value is similarly generated in the case that a deformation is generated in the pattern by a deviation between the electron beam shots. As used herein, the output value means the output value of an electric image signal to which photoelectric conversion is performed by an image sensor in a process in which the image of the light, which is transmitted from or reflected from the sample after the sample is irradiated by a lighting optical system, is formed on the image sensor through the imaging optical system and used as the optical image data.

In the identical pattern, the fluctuation of the output value exerts an identical tendency irrespective of the position of the optical image data. Therefore, optical image data having the identical pattern are acquired while a condition of the optical system is changed, and variations of the output values in the optical image data are compared to each other. The focal position can properly be detected in the repetitive pattern, in which the period is less than or equal to the resolution of the optical system, by finding the condition at the maximum variation. Specifically, the focal position where the variation reaches the maximum is used as a reference focal position, and an optimum focal position is set based on the reference focal position. For example, the variation of the output value is expressed by a variance or a standard deviation of gradation values. Hereinafter, embodiments of the present invention will be described in detail with reference to the drawings.

First Embodiment

Figure 1:
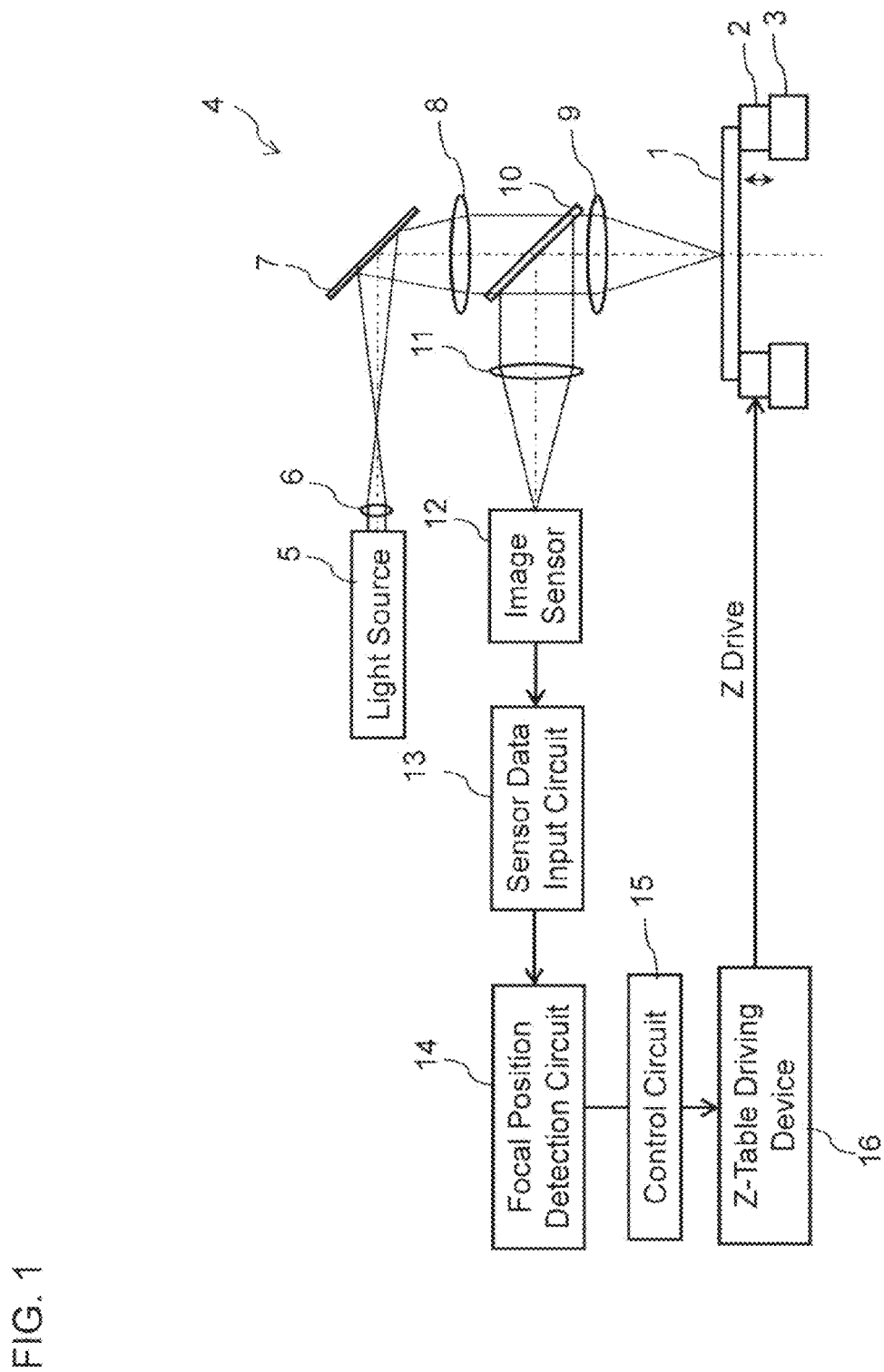
FIG. 1 is a view illustrating a configuration of a focal position detection apparatus according to a first embodiment.

FIG. 1 is a view illustrating a configuration of a focal position detection apparatus according to a first embodiment.

Referring to FIG. 1, a sample 1 is placed on a Z-table 2 that is vertically movable. The Z-table 2 is also horizontally movable by an XY-table 3. The repetitive pattern such as the line and space pattern and a hole pattern, namely, the regular pattern having periodic repetition is formed in the sample 1. A master pattern and a daughter pattern, which are used in a nanoimprint technology, can be cited as an example of the sample 1.

Figure 11:
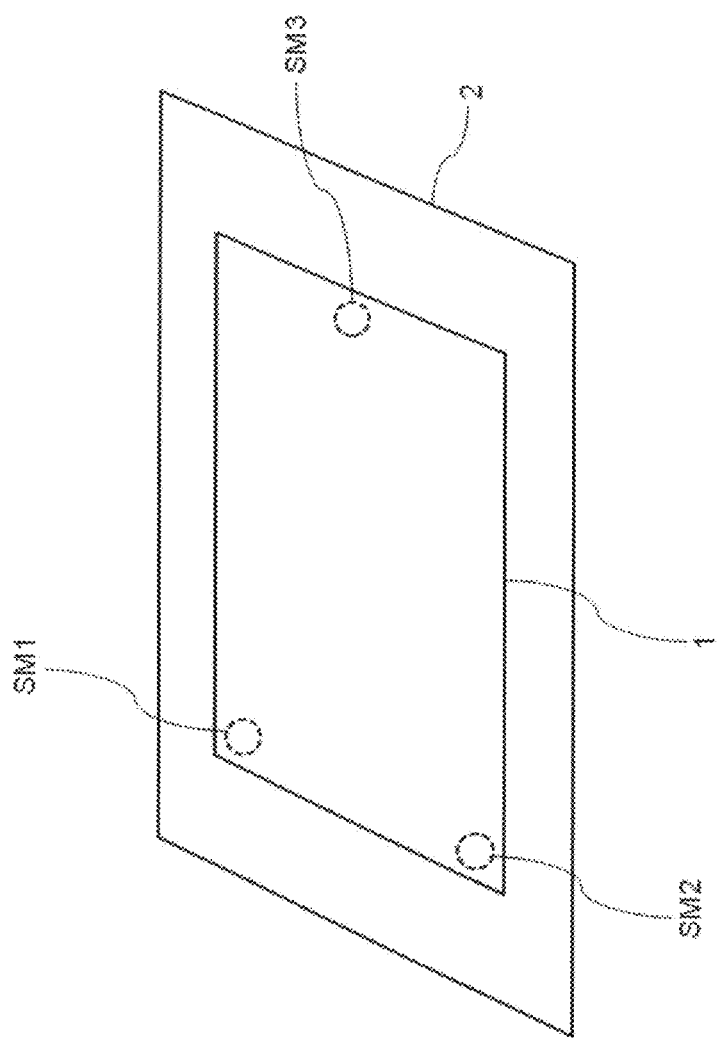
FIG. 11 is a view in which the support members supporting the sample at three points.

Preferably the sample 1 is supported at three points by support members provided in the Z-table 2. In the case the sample 1 is supported at four points, it is necessary to accurately adjust a level with respect to the support member. When the level is insufficiently adjusted, there is a risk of deforming the sample 1. On the other hand, in the three-point support, the sample 1 can be supported while the deformation of the sample 1 is minimized. For example, the support member is constructed using a ball point having a spherical head surface. For example, as illustrated in FIG. 11, among three support members (SM1, SM2, and SM3), the two support members (SM1 and SM2) are in contact with the sample 1 at two corners among four corners of the sample 1, in which the two corners are adjacent to each other and not diagonal. Among the three support members (SM1, SM2, and SM3), the remaining support member (SM3) is disposed in an area between two corners on which the two support members (SM1 and SM2) are not disposed.

As illustrated in FIG. 1, an optical system 4 is disposed above the sample 1.

In the optical system 4, a light source 5 emits light toward the sample 1 in order to acquire optical image data of the sample 1. The line width of the main pattern formed in the sample 1 can be set to 100 nm or less, and the light source 5 that emits DUV (Deep Ultraviolet radiation) light can be used.

The light emitted from the light source 5 is transmitted through a lens 6, and an orientation of the light is changed by a mirror 7. Then, the light is transmitted through a lens 8, and focused on the sample 1 by a lens (an objective lens) 9. The lens 9 of the first embodiment corresponds to the first lens of the present invention.

The orientation of the light reflected by the sample 1 is changed by a half mirror 10. Then a lens (an imaging lens) 11 forms an image of the light on an image sensor 12. Therefore, optical image data of the pattern of the sample 1 is generated. The lens 11 of the first embodiment corresponds to the second lens of the present invention.

A resolution limit of the optical system 4, namely, the resolution limit ($R=\lambda/2NA$) determined by a wavelength ($\lambda$) of the light from the light source 5 and a numerical aperture (NA) of the lens 11 is a value in which the pattern formed on the sample 1 is not resolved.

Alternatively, the image sensor is disposed below the sample 1, and the image of the light transmitted through the sample 1 may be formed on the image sensor.

Figure 2:
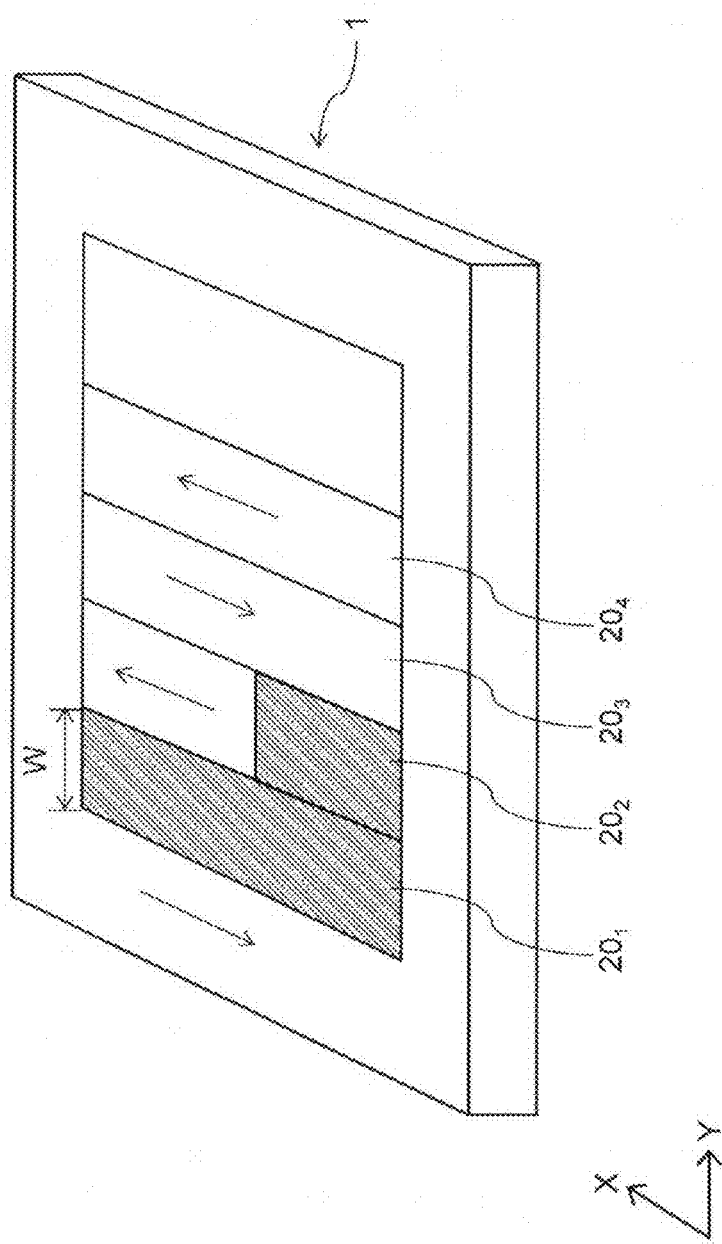
FIG. 2 is a view illustrating a procedure to acquire the optical image data of the pattern formed on the sample.

FIG. 2 is a view illustrating a procedure to acquire the optical image data of the pattern formed on the sample 1.

As illustrated in FIG. 2, an evaluation area on the sample 1 is virtually divided into a plurality of reed-shaped frames $20_1$, $20_2$, $20_3$, $20_4$, . . . . A driving device (not illustrated)

controls operation of the XY-table 3 in FIG. 1 such that the frames $20_1$, $20_2$, $20_3$, $20_4$, . . . are continuously scanned. Specifically, the optical image data of the sample 1 is acquired while the XY-table 3 moves in the X-direction. The image having a scanning width W in FIG. 2 is continuously input to the image sensor 12. That is, the image in the second frame $20_2$ is acquired after the image in the first frame $20_1$ is acquired. In this case, the optical image data is acquired while the XY-table 3 is moved in a direction opposite to the case that the image in the first frame $20_1$ is acquired, and the image having the scanning width W is continuously input to the image sensor 12. In the case that the image in the third frame $20_3$ is acquired, the XY-table 3 moves in the direction opposite to the direction in which the image in the second frame $20_2$ is acquired, namely in the direction in which the image in the first frame $20_1$ is acquired. A shaded area in FIG. 2 schematically expresses the area where the optical image data has already been acquired in the above manner.

The image sensor 12 performs photoelectric conversion to the pattern image formed on the image sensor 12 in FIG. 1, and a sensor circuit (not illustrated) performs A/D (analog to digital) conversion to the pattern image. For example, a line sensor in which CCD cameras that are of the image capturing elements are arrayed in line is used as the image sensor 12. A TDI (Time Delay Integration) sensor can be cited as an example of the line sensor. The TDI sensor captures the pattern image on the sample 1 while the XY-table 3 moves continuously in the X-axis direction.

Figure 3:
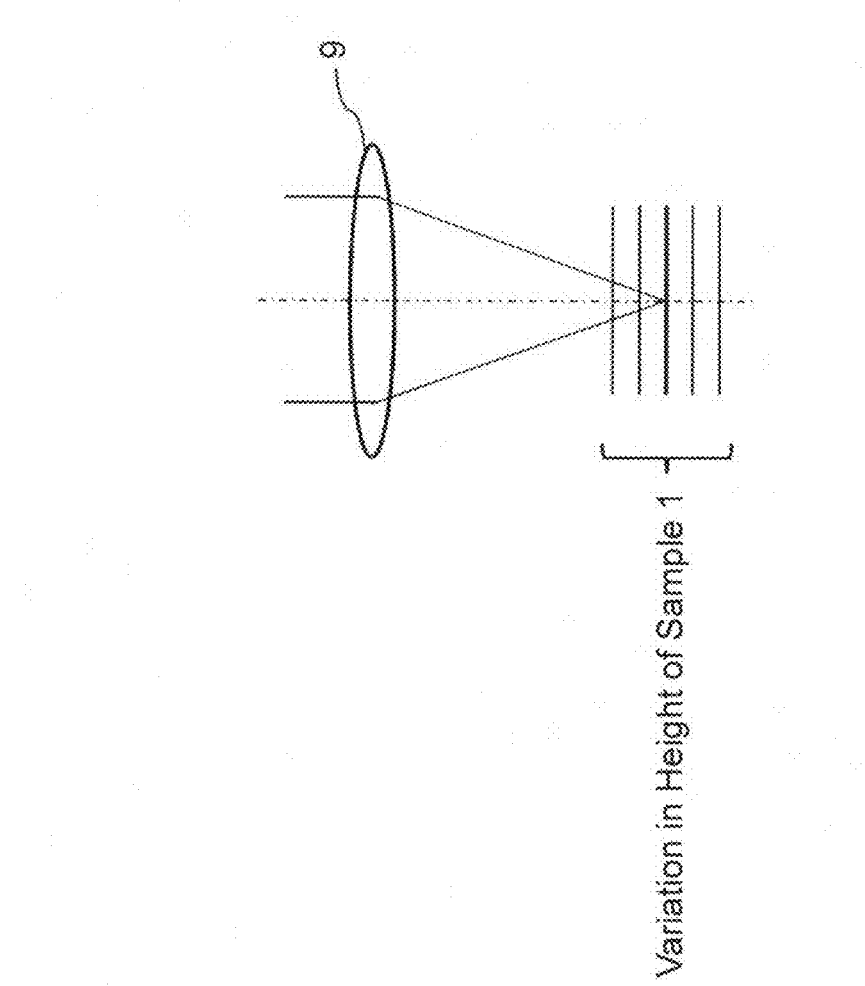
FIG. 3 illustrates the optical image data being acquired while the level of the sample is varied.

In a focal position detection method of the first embodiment, at least two optical image data are acquired while the focal position between the sample 1 and the optical system 4 is changed. Specifically, as illustrated in FIG. 3, the optical image data is acquired while the level of the sample 1 is varied. Referring to FIG. 1, because the sample 1 is placed on the vertically movable Z-table 2, the distance from the sample 1 to the lens 9 changes by changing the vertical position of the Z-table 2, thereby changing the focal position between the sample 1 and the optical system 4. For example, the first optical image data is acquired while the Z-table 2 is located at a predetermined position, and the position of the Z-table 2 is moved to acquire the second optical image data.

Alternatively, the focal position between the sample 1 and the optical system 4 may be changed by changing the distance between the lens 11 and the image sensor 12. However, in the case the distance is fixed to a value determined at a design stage, it is only necessary to consider the distance between the lens 9 and the sample 1.

The image sensor 12 performs the photoelectric conversion to the pattern image formed on the image sensor 12, and then a sensor data input circuit 13 performs the A/D conversion to the pattern image. Then the data is transmitted from the sensor data input circuit 13 to a focal position detection circuit 14. The focal position detection circuit 14 of the first embodiment corresponds to the focal position detector of the present invention.

In the focal position detection circuit 14, the variations of the output values in the optical image data are compared to each other to detect the optimum focal position between the sample 1 and the optical system 4.

For example, as described above, optical image data is acquired while the distance between the sample 1 and the lens 9 is changed by adjusting the level of the Z-table 2. Then, a gradation value is provided in each pixel with respect to the optical image data, and the variance or the standard deviation of the gradation values is obtained in each optical image data. Then a relationship between the focal position and the variance or the standard deviation is acquired to obtain the focal position where the variance or the standard deviation reaches the maximum. The obtained focal position is the optimum focal position, namely, the focal position where the contrast of the sample 1 reaches the maximum.

Figure 4:
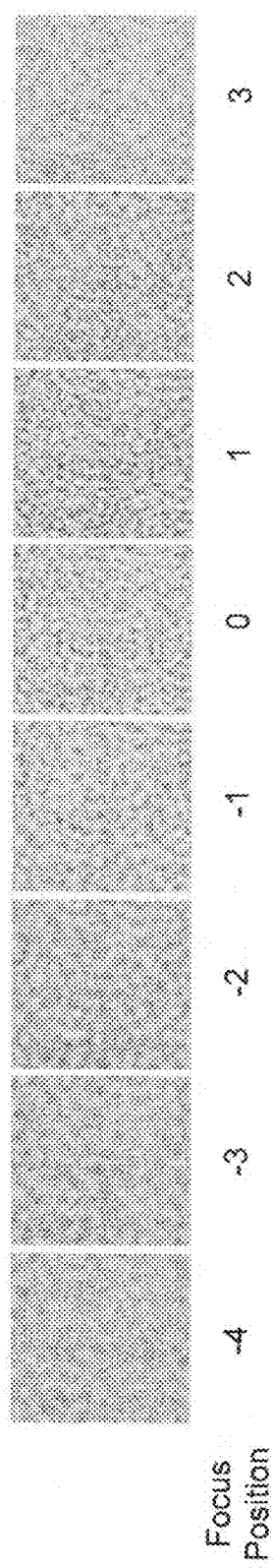
FIG. 4 illustrates an example of the optical image that is captured while the focal position between the sample and the optical system is changed with respect to the repetitive pattern in which the period is less than or equal to the resolution of the optical system.

FIG. 4 illustrates an example of the optical image that is captured while the focal position between the sample and the optical system is changed with respect to the repetitive pattern in which the period is less than or equal to the resolution of the optical system. The focal position in FIG. 4 is expressed by a relative value, and the actual optical image is acquired by deviating the focal position by, for example, 0.1 μm. A shading variation (a variation of a gradation value) seen in optical image data is caused by the fluctuation in line width or edge roughness of the repetitive pattern.

Figure 5:
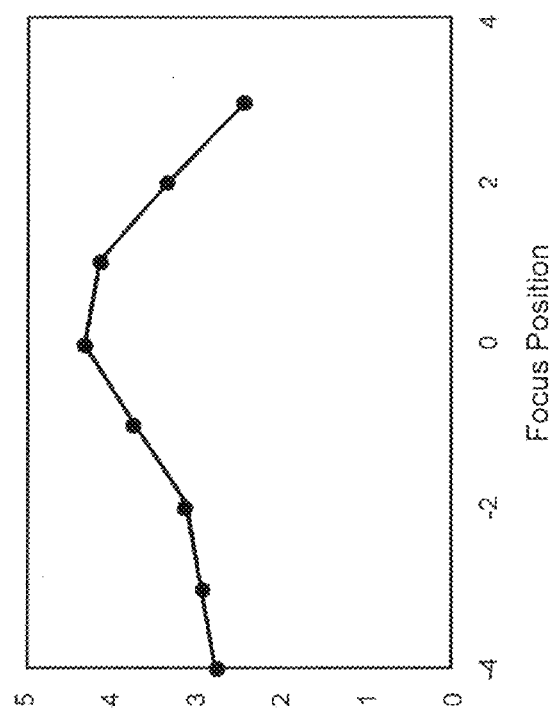
FIG. 5 illustrates a relationship between the focal position and the standard deviation of the gradation values obtained from the optical images in FIG. 4.

FIG. 5 illustrates a relationship between the focal position and the standard deviation of the gradation values obtained from the optical images in FIG. 4. Referring to FIG. 4, the shading variation changes largely between the focal positions of 0 and 1. Accordingly, in FIG. 5, the standard deviation of the gradation values also expresses the large value between the focal positions of 0 and 1. The focal position of 0 where the standard deviation of the gradation values reaches the maximum is the position where the contrast of the optical image data reaches the maximum, namely, the optimum focal position. In the defect inspection, sometimes S/N is further improved when the inspection is made while a given offset is intentionally applied to the optimum focal position where the contrast of the optical image data reaches the maximum. In this case, the optimum focal position where the contrast of the optical image data reaches the maximum is obtained, and the optimum focal position is set in the inspection in which correction is performed by the offset amount.

Referring to FIG. 1, the information on the focal position detected by the focal position detection circuit 14 is transmitted to a control circuit 15. The control circuit 15 controls a Z-table driving device 16 based on the transmitted information, and the control circuit 15 adjusts the level of the Z-table 2 such that the sample 1 is located at the optimum focal position with respect to the optical system 4.

As described above, according to the first embodiment, optical image data is acquired while the optical condition is changed, the variations of the output values are compared to each other, and the focal position can properly be detected irrespective of the change in pressure or temperature by finding the optical condition that maximizes the variation. Then the defect of the repetitive pattern in which the period is less than or equal to the resolution of the optical system can be detected by checking a gradation value distribution map of the optical image data. That is, when the edge roughness is partially increased, when the pattern is partially lacked, or when the line width is partially narrowed, the disturbance is generated in the regularity to change the gradation value. Therefore, the partially-increased edge roughness, the partially-lacked pattern, and the partially-narrowed line width can be detected as the defect.

Second Embodiment

Figure 6:
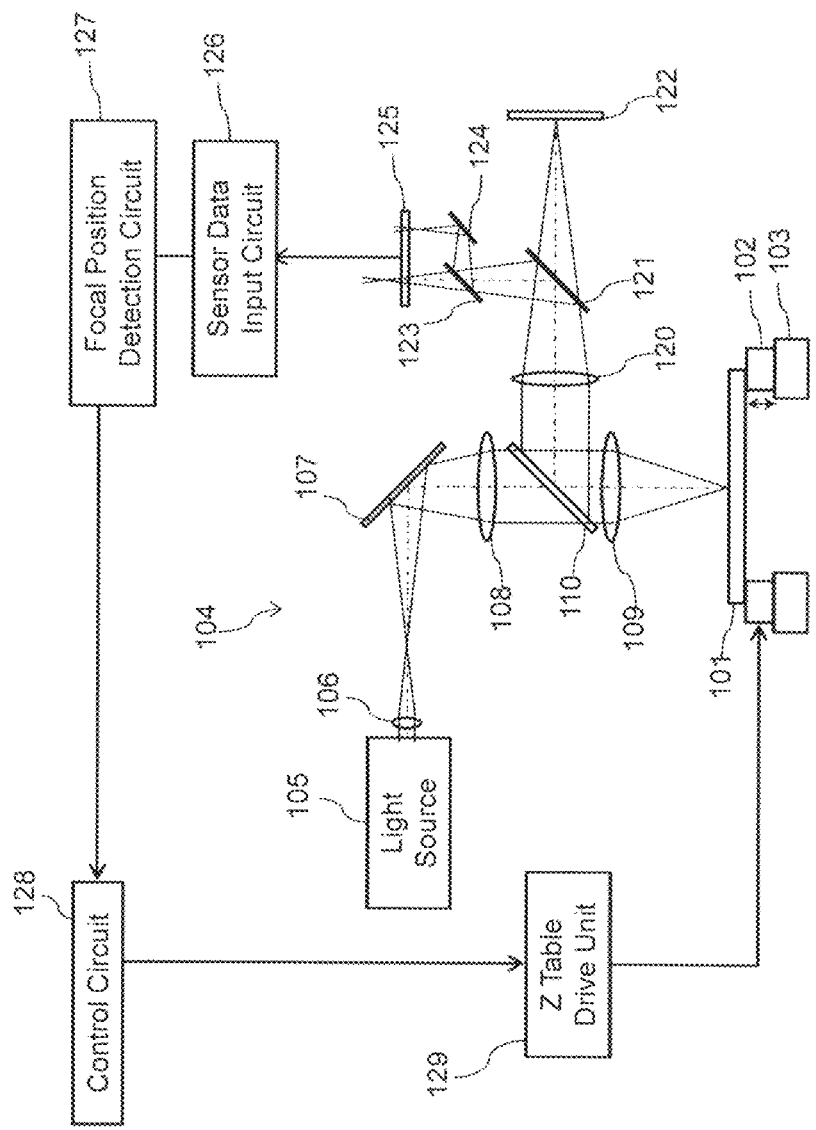
FIG. 6 is a view illustrating a configuration of a focal position detection apparatus according to the second embodiment.

FIG. 6 is a view illustrating a configuration of a focal position detection apparatus according to a second embodiment.

Referring to FIG. 6, a sample 101 is placed on a Z-table 102 that is vertically movable. The Z-table 102 is also horizontally movable by an XY-table 103. The repetitive pattern such as the line and space pattern and the hole pattern, namely, the regular pattern having periodic repetition is formed in the sample 101. The master pattern and the daughter pattern, which are used in the nanoimprint technology, can be cited as an example of the sample 101.

Preferably the sample 101 is supported at three points by the support members provided in the Z-table 102. In the case that the sample 101 is supported at four points, it is necessary to accurately adjust the level with respect to the support member. When the level is insufficiently adjusted, there is a risk of deforming the sample 101. On the other hand, in the three-point support, the sample 101 can be supported while the deformation of the sample 101 is minimized. For example, the support member is constructed by the ball point having the spherical head surface. For example, as illustrated in FIG. 11, among the three support members (SM1, SM2, and SM3), the two support members (SM1 and SM2) are in contact with the sample 101 at the two corners among the four corners of the sample 101, which the two corners are adjacent to each other and not diagonal. Among the three support members (SM1, SM2, and SM3), the remaining support member (SM3) is disposed in the area between the two corners on which the two support members (SM1 and SM2) are not disposed.

As illustrated in FIG. 6, an optical system 104 is disposed above the sample 101. In the optical system 104, a light source 105 emits the light toward the sample 101 in order to acquire the optical image data of the sample 101. The line width of the main pattern formed in the sample 101 can be set to 100 nm or less, and the light source 105 that emits the DUV (Deep Ultraviolet radiation) light can be used.

The light emitted from the light source 105 is transmitted through a lens 106, and the orientation of the light is changed by a mirror 107. Then, the light is transmitted through a lens 108, and focused on the sample 101 by a lens (the objective lens) 109. The lens 109 of the second embodiment corresponds to the first lens of the present invention.

The orientation of the light reflected from the sample 101 is changed by a half mirror 110. Then after the light transmits through a lens (the imaging lens) 120, part of that light transmits through a half mirror 121 and forms the image of the light on an image sensor (a first image sensor) 122. Therefore, the optical image data of the pattern of the sample 101 is generated. The resolution limit of the optical system 104, namely, the resolution limit (R=λ/2NA) determined by the wavelength (λ) of the light from the light source 105 and the numerical aperture (NA) of the lens 120 is the value in which the pattern formed on the sample 101 is not resolved. The lens 120 of the second embodiment corresponds to the second lens of the present invention.

Specifically, the image sensor 122 performs the photoelectric conversion to the pattern image formed on the image sensor 122, and the sensor circuit (not illustrated) performs the A/D conversion to the pattern image. For example, the line sensor in which the CCD cameras that are of the image capturing elements are arrayed in line is used as the image sensor 122. The TDI (Time Delay Integration) sensor can be cited as an example of the line sensor. The TDI sensor captures the pattern image on the sample 101 while the XY-table 103 moves continuously in the X-axis direction. The procedure to acquire the optical image data is similar to that in FIG. 2 of the first embodiment.

Part of the light transmitted through the lens 120 is divided by a half mirror 121 that is of the optical path splitting unit, and taken out in the direction different from the image sensor 122. That is, part of the light transmitted through the lens 120 is incident to the image sensor 122 through the half mirror 121, and the half mirror 121 reflects the remaining part of the light. Then the light is further divided into two optical paths by a half mirror 123 and a mirror 124. Specifically, part of the light reflected by the half mirror 121 is transmitted through the half mirror 123. The mirror 124 reflects the remaining part of the light reflected from the half mirror 121. The light transmitted through the half mirror 123 and the light reflected by the mirror 124 exits in the identical direction. A focal position detecting image sensor (a second image sensor) 125 is disposed on the optical paths of the light transmitted through the half mirror 123 and the light reflected by the mirror 124.

The image sensor 125 detects two pieces of image information on the light incident to the image sensor 125. One is the image information in the case that a focal point is located ahead the imaging plane (a focal point ahead of the pattern), and the other is the image information in the case that the focal point is located behind the imaging plane (focal point behind the pattern). Referring to FIG. 6, the image information on the focal point behind the pattern is obtained from the light transmitted through the half mirror 123. On the other hand, the image information on the focal point ahead of the pattern is obtained from the light reflected from the mirror 124. The image at the focal point behind the pattern and the image at the focal point ahead of the pattern are not formed on the image sensor.

Figure 7:
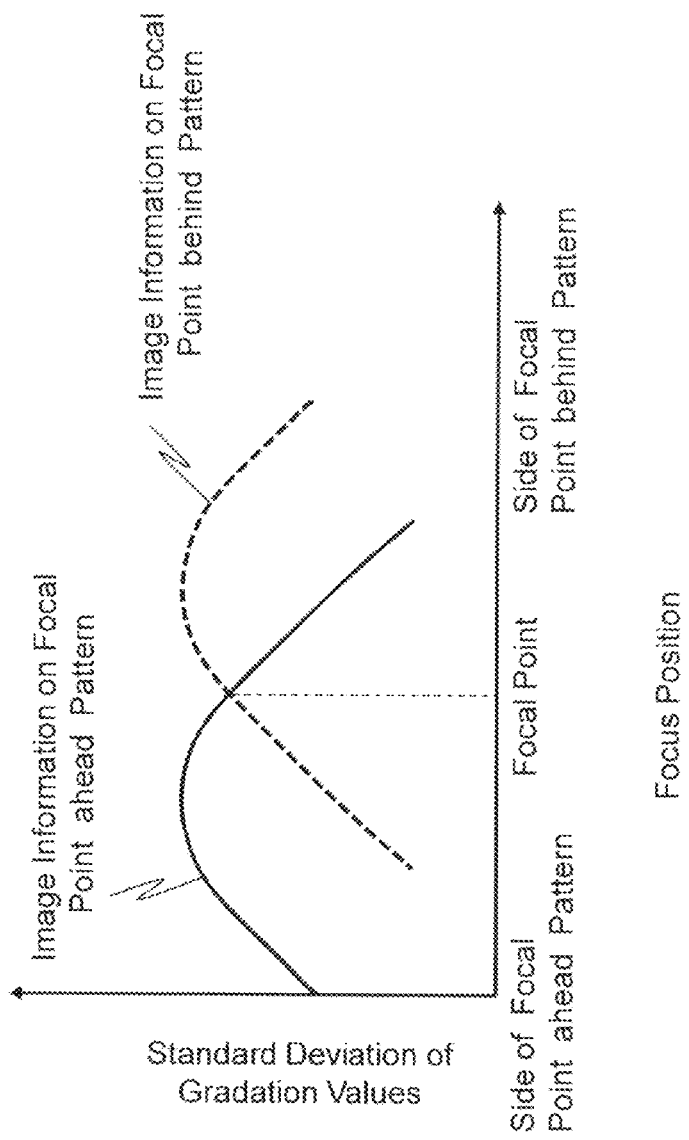
FIG. 7 illustrates comparison between the image information on the focal point ahead of the pattern and the image information on the focal point behind the pattern according to the second embodiment.

FIG. 7 illustrates comparison between the image information on the focal point ahead of the pattern and the image information on the focal point behind the pattern. In FIG. 6, the focal point of the light transmitted through the half mirror 123 is located behind the image sensor 125. The optical image data is acquired by changing the focal position of the light transmitted through the half mirror 123, and the standard deviations of the gradation values are compared to each other. The result is indicated by a dotted line in FIG. 7. On the other hand, the focal point of the light reflected from the mirror 124 in FIG. 6 is located ahead the image sensor 125. The optical image data is acquired by changing the focal position of the light reflected from the mirror 124, and the standard deviations of the gradation values are compared to each other. The result is indicated by a solid line in FIG. 7. The focal position of each piece of light is changed by adjusting the level of the Z-table 102. For example, each optical image data is acquired by deviating the focal position by 0.1 μm.

The standard deviation of the gradation value in each piece of image information in FIG. 7 is caused by the fluctuation in line width or edge roughness of the repetitive pattern formed on the sample 101. When the focal position between the optical system 104 and the sample 101 is located ahead the image sensor 125, the standard deviation of the gradation value increases on the side of the focal point ahead of the pattern. On the other hand, when the focal position is located behind the image sensor 125, the standard deviation of the gradation value increases on the side of the focal point behind the pattern. The focal position between the optical system 104 and the sample 101 is located on the image sensor 122, when the standard deviation of the gradation value on the side of the focal point ahead of the pattern is equal to the standard deviation of the gradation value on the side of the focal point behind the pattern, namely, when the focal position on the side of the focal point ahead of the pattern and the focal position on the side of the behind the pattern are deviated from the image sensor 125 by the identical distance in the directions opposite to each other. This is the optimum focal position, and the contrast reaches the maximum.

Figure 8:
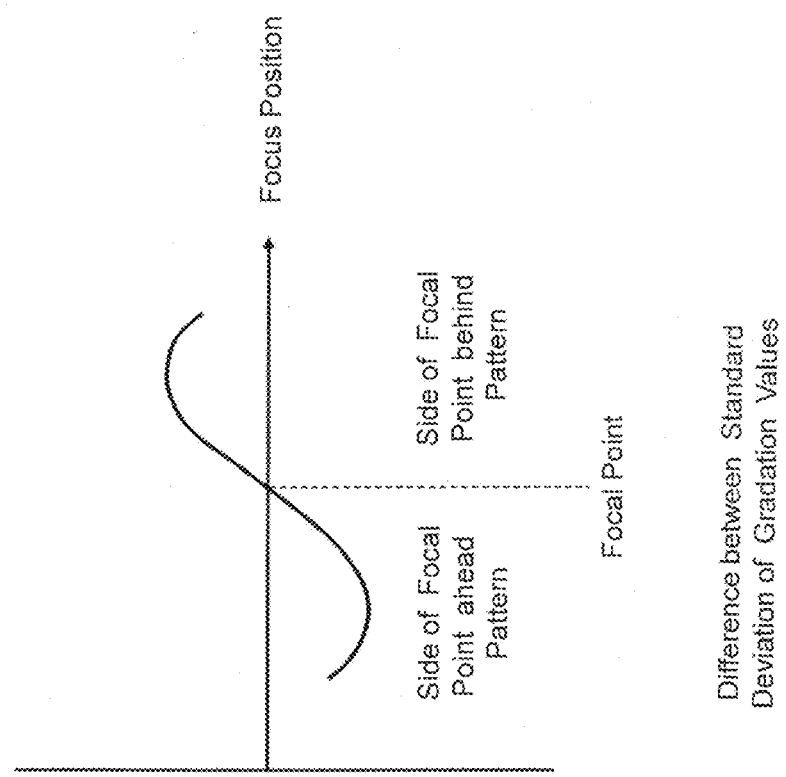
FIG. 8 is a graph in which a difference between the standard deviation of the gradation value on the side of the focal point ahead of the pattern and the standard deviation of the gradation value on the side of the focal point behind the pattern is plotted to the focal position according to the second embodiment.

FIG. 8 is a graph in which a difference between the standard deviation of the gradation value on the side of the focal point ahead of the pattern and the standard deviation of the gradation value on the side of the focal point behind the pattern is plotted. The focal position where the difference becomes zero is the focal point.

Thus, in the second embodiment, optical image data is acquired on each of the side of the focal point ahead of the pattern and the side of the focal point behind the pattern while the focal position between the optical system and the sample is changed. The obtained optical image data is transmitted from the image sensor 125 in FIG. 6 to a sensor data input circuit 126. The image sensor 125 performs the photoelectric conversion to the pattern image, and the sensor data input circuit 126 performs the A/D conversion to the pattern image. Then the data is transmitted from the sensor data input circuit 126 to a focal position detection circuit 127. The focal position detection circuit 127 of the second embodiment corresponds to the focal position detector of the present invention.

In the focal position detection circuit 127, the variation of the output value in the optical image data on each of the side of the focal point ahead of the pattern and the side of the focal point behind the pattern is obtained, and the focal position is properly obtained from the difference between the variations. As described above, for example, the output value is expressed by the gradation value and the variation is expressed by the variance or the standard deviation. The focal position where the difference becomes zero is the proper focal position.

Figure 9:
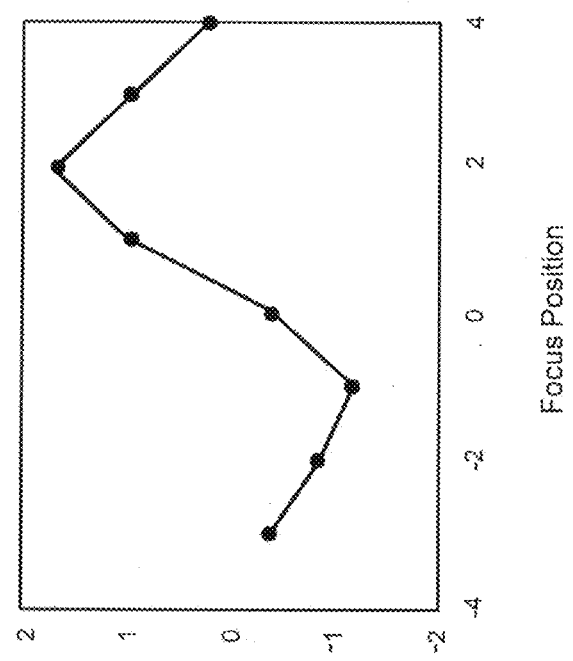
FIG. 9 is a view illustrating an example in which the difference in standard deviation of the gradation value between the side of the focal point ahead of the pattern and the side of the focal point behind the pattern is plotted to the focal position according to the second embodiment.

FIG. 9 is a view illustrating an example in which the difference in standard deviation of the gradation value between the side of the focal point ahead of the pattern and the side of the focal point behind the pattern is obtained from the optical image data obtained by the image sensor 125 in FIG. 6 and plotted with respect to the focal position. The focal position in FIG. 9 is expressed by a relative value, and the actual optical image is acquired by deviating the focal position by, for example, 0.1 μm. In FIG. 9, the focal position of 0 where the difference becomes zero is the position where the contrast of the optical image data reaches the maximum, namely, the optimum focal position.

As illustrated in FIG. 6, the information on the focal position detected by the focal position detection circuit 127 is transmitted to a control circuit 128. The control circuit 128 controls a Z-table driving device 129 based on the transmitted information, and the control circuit 128 adjusts the level of the Z-table 102 such that the sample 101 is at the optimum focal position with respect to the located optical system 104.

As described above, according to the second embodiment, optical image data is acquired on each of the side of the focal point ahead of the pattern and the side of the focal point behind the pattern while the focal position is changed, the difference in variation of the output value between the optical image data is obtained, and the focal position where the difference becomes zero is found. Therefore, the optimum focal position can be detected irrespective of the change in pressure or temperature. Then the defect of the repetitive pattern in which the period is less than or equal to the resolution of the optical system can be detected by checking the gradation value distribution map of the optical image data. That is, when the edge roughness is partially increased, when the pattern is partially lacked, or when the line width is partially narrowed, the disturbance is generated in the regularity to change the gradation value. Therefore, the partially-increased edge roughness, the partially-lacked pattern, and the partially-narrowed line width can be detected as the defect.

Third Embodiment

Figure 10:
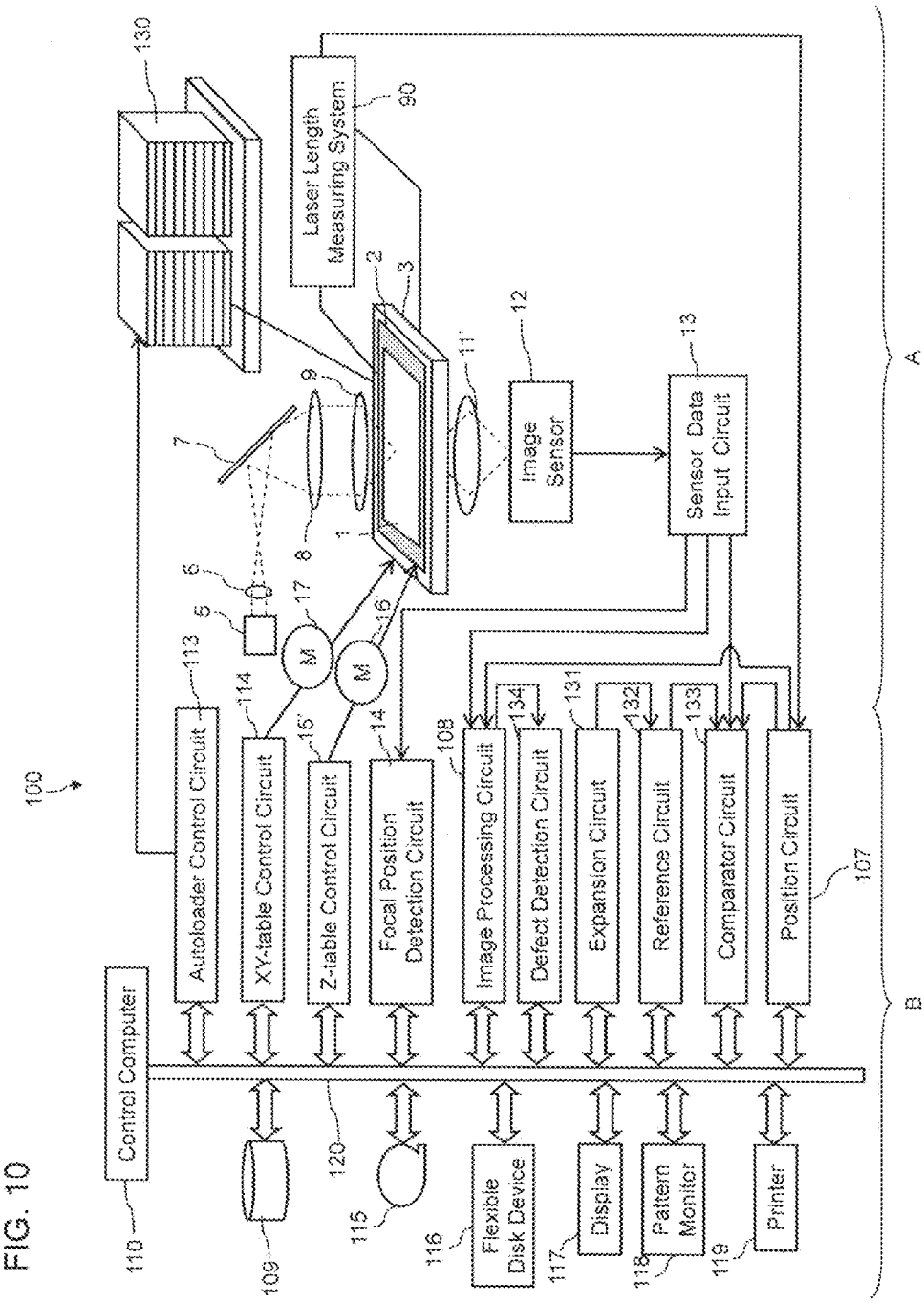
FIG. 10 is a view illustrating a configuration of an inspection apparatus according to a third embodiment.

FIG. 10 is a view illustrating a configuration of an inspection apparatus 100 according to a third embodiment. As illustrated in FIG. 10, the inspection apparatus 100 includes an optical image acquisition unit A and a controller B. In FIG. 10, the component identical to that in FIG. 1 is designated by the numeral identical to that in FIG. 1.

The optical image acquisition unit A includes an optical system, which is constructed by the light source 5, lenses 6, 8, 9, and 11', the mirror 7, the image sensor 12, and the sensor data input circuit 13. The optical image acquisition unit A includes the vertically movable Z-table 2, the horizontally (an X-direction and a Y-direction) movable XY-table 3, a laser length measuring system 90, and an autoloader 130. The XY-table 3 may have a structure that is movable in a rotating direction (θ-direction).

The sample 1 that becomes an inspection target is placed on the Z-table 2. The Z-table 2 is provided on the XY-table 3, and the Z-table 2 can move horizontally together with the XY-table 3. At this point, the repetitive pattern such as the line and space pattern, namely, the regular patterns having periodic repetition is formed on the sample 1. A template used in the nanoimprint technology can be cited as an example of the sample 1.

Preferably the sample 1 is supported at the three points by the support members provided in the Z-table 2. In the case that the sample 1 is supported at the four points, it is necessary to accurately adjust the level with respect to the support member. When the level is insufficiently adjusted, there is the risk of deforming the sample 1. On the other hand, in the three-point support, the sample 1 can be supported while the deformation of the sample 1 is minimized. For example, the support member is constructed by the ball point having the spherical head surface. For example, as illustrated in FIG. 11, among the three support members (SM1, SM2, and SM3), the two support members (SM1 and SM2) are in contact with the sample 1 at two corners among four corners of the sample 1, which the two corners are adjacent to each other and not diagonal. Among the three support members (SM1, SM2, and SM3), the remaining support member (SM3) is disposed in an area between two corners on which the two support members (SM1 and SM2) are not disposed.

The light source 5 emits the light toward the sample 1 in order to acquire the optical image data of the sample 1. The wavelength of the light emitted from the light source 5 is greater than or equal to twice a pattern pitch. The inspection apparatus 100 is suitable to the inspection of the ultra-fine pattern in which the line width is less than or equal to 100 nm, and the light source that emits the DUV (Deep Ultraviolet radiation) light is preferably used as the light source 5. The use of the DUV light can relatively easily construct the optical system, and inspect the fine pattern with high throughput compared with the use of an EB (Electron Beam).

The light emitted from the light source 5 is transmitted through the lens 6, and the orientation of the light is changed by the mirror 7. Then, the light is transmitted through the lens 8, and focused on the sample 1 by the lens (the objective lens) 9. The lens 9 of the third embodiment corresponds to the first lens of the present invention.

The image of the light transmitted through the sample 1 is formed on the image sensor 12 by a lens (imaging lens) 11'. Therefore, the optical image data of the pattern of the sample 1 is generated. The procedure to acquire the optical image data is similar to that in FIG. 2 of the first embodiment. The lens 11' of the third embodiment corresponds to the second lens of the present invention.

The resolution limit of the optical system in the inspection apparatus 100, namely, the resolution limit (R=λ/2NA) determined by the wavelength (λ) of the light from the light source 5 and the numerical aperture (NA) of the lens 11' is the value in which the pattern formed on the sample 1 is not resolved.

Alternatively, like the first embodiment, the image sensor is disposed above the sample 1, and the image of the light reflected from the sample 1 may be formed on the image sensor.

The controller B in FIG. 10 will be described below.

In the controller B, a control computer 110 that controls the whole inspection apparatus 100 is connected to a position circuit 107, an image processing circuit 108, the focal position detection circuit 14, an expansion circuit 131, a reference circuit 132, a comparator circuit 133, a defect detection circuit 134, an autoloader control circuit 113, a Z-table control circuit 15', an XY-table control circuit 114, a magnetic disk device 109, a magnetic tape device 115, a flexible disk device 116, a display 117, a pattern monitor 118, and a printer 119 through a bus 120 that constitutes a data transmission path. The magnetic disk device 109, the magnetic tape device 115, and the flexible disk device 116 are examples of the storage device. The image processing circuit 108 corresponds to the image processor of the present invention, the focal position detection circuit 14 corresponds to the focal position detector of the present invention, and the defect detection circuit 134 corresponds to the defect detector of the present invention.

The Z-table 2 is driven by a motor 16' that is controlled by the Z-table control circuit 15'. The Z-table control circuit 15' corresponds to the control circuit 15 in FIG. 1, and the motor 16' corresponds to the Z-table driving device 16 in FIG. 1. The XY-table 3 is driven by a motor 17 that is controlled by the XY-table control circuit 114. For example, a linear motor can be used as the motors.

As described above, the optical image acquisition unit A in FIG. 10 acquires the optical image data of the sample 1. An example of the specific method for acquiring the optical image data is as follows.

The sample 1 is placed on the vertically movable Z-table 2. The Z-table 2 is also horizontally movable by the XY-table 3. The movement position of the XY-table 3 is measured by the laser length measuring system 90 and transmitted to the position circuit 107. The sample 1 on the XY-table 3 is automatically conveyed from the autoloader 130 that is driven by the autoloader control circuit 113, and automatically discharged after the inspection.

The light source 5 irradiates the sample 1 with the inspecting light. The light emitted from the light source 5 is transmitted through the lens 6, the orientation of the light is changed by the mirror 7, and the light is focused on the sample 1 by the lenses 8 and 9. The distance between the lens 9 and the sample 1 is adjusted by vertically moving the Z-table 2.

The image of the light, which is emitted from the light source 5 and transmitted through the sample 1, is formed as the optical image on the image sensor 12 through the lens 11'. The distance between the lens 11' and the image sensor 12 is determined at a design stage of the inspection apparatus 100.

The procedure to acquire the optical image data in the inspection area of the sample 1 is similar to that in FIG. 2. The photoelectric conversion is performed to the pattern image formed on the image sensor 12, and the A/D conversion is also performed to the pattern image by the sensor data input circuit 13. For example, the line sensor in which the CCD cameras that are of the image capturing elements are arrayed in line is used as the image sensor 12. The TDI (Time Delay Integration) sensor can be cited as an example of the line sensor. The TDI sensor captures the pattern image on the sample 1 while the XY-table 3 moves continuously in the X-axis direction.

The focal position between the sample 1 and the optical system are determined similarly to the first embodiment.

At least two optical image data are acquired while the distance between the sample 1 and the lens 9 is changed.

Specifically, referring to FIG. 10, because the sample 1 is placed on the vertically movable Z-table 2, the distance between the sample 1 and the lens 9 can change by changing the vertical position of the Z-table 2. For example, the first optical image data is acquired while the Z-table 2 is located at a predetermined position, and the position of the Z-table 2 is moved to acquire the second optical image data.

The image sensor 12 performs the photoelectric conversion to the pattern image formed on the image sensor 12, and then a sensor data input circuit 13 performs the A/D conversion to the pattern image. Then the data is transmitted from the sensor data input circuit 13 to the focal position detection circuit 14.

In the focal position detection circuit 14, the variations of the output values in the optical image data are compared to each other to detect the optimum focal position between the sample 1 and the lens 9, namely, the optimum focal position.

For example, as described above, optical image data is acquired while the focal position is changed by adjusting the level of the Z-table 2. Then, the gradation value is provided in each pixel with respect to the optical image data, and the variance or the standard deviation of the gradation values is obtained in each optical image data. Then the relationship between the focal position and the variance or the standard deviation is acquired to obtain the focal position where the variance or the standard deviation reaches the maximum. The obtained focal position is the optimum focal position.

The information (for example, a displacement amount from the present focal position to the focusing position) on the focal position detected by the focal position detection circuit 14 is transmitted to the Z-table control circuit 15'. The Z-table control circuit 15' controls the motor 16' based on the transmitted information, and the control circuit 15' adjusts the level of the Z-table 2 such that the sample 1 is located at the optimum focal position with respect to the lens 9.

The optical image data is transmitted from the sensor data input circuit 13 to the image processing circuit 108.

In the image processing circuit 108, the pixel data in the optical image data obtained at the optimum focal position is expressed by the gradation value in each pixel. For example, using a gray scale having 256 levels of the gradation values, one of values of a 0 level to a 255 level is provided to each pixel. The inspection area of the sample 1 is divided into predetermined unit regions, and at least one of either an average gradation value of the unit regions or the variation of the gradation value in the unit region is determined. For example, the predetermined unit region may be set to the area of 25 μm by 25 μm.

The information on the gradation value obtained by the image processing circuit 108 is transmitted to the defect detection circuit 134. The defect detection circuit 134 detects the defect of the sample 1 based on at least one of either the average gradation value or the variation of the gradation value.

For example, the average gradation value is correlated with an average value of the pattern line widths. The variation of the gradation value in each unit region is correlated with the irregularity (the roughness) at the pattern edge. For example, a relational expression between the line width and the gradation value is written by obtaining the value of the line width measured with a length measuring SEM and the gradation value of the optical image data with respect to the predetermined pattern. A user can convert the average gradation value into the average value of the line widths in the unit region using the relational expression. Even if the average gradation value is kept constant, it can be considered that the pattern edge has the large irregularity (the large roughness) in the case of the large variation of the gradation value in each unit region, namely, the large standard deviation of the gradation value. A degree of evenness of the pattern in the sample 1 can be understood to detect the defect, when at least one of either a map expressing a distribution of the line width average value acquired from the average gradation value or a map expressing a distribution of the pattern edge irregularity (the roughness) acquired from the variation of the gradation value in each unit region is produced.

For example, the map is stored in the magnetic disk device 109 in FIG. 10. When the fluctuation of the line width or the large variation of the irregularity at the pattern edge is understood from the map, the data stored in the magnetic disk device 109 can be fed back to a photolithography condition in forming the pattern of the sample 1. For example, when the line width fluctuates, the fluctuation of the line width can be decreased on the wafer by optimizing a resist exposure condition and an etching condition based on the data.

In the inspection apparatus 100 in FIG. 10, the inspection can be performed by a die-to-database system. The die-to-database system is a technique, in which reference image data is generated based on design pattern data and compared to the optical image data obtained by capturing the image of the pattern.

Referring to FIG. 10, the design pattern data that constitutes database-system reference data is stored in the magnetic disk device 109, read with the progress of the inspection, and transmitted to the expansion circuit 131. The expansion circuit 131 converts the design pattern data into the image data (design pixel data). Then, the image data is transmitted to the reference circuit 132, and used to generate the reference image data. The generated reference image data is transmitted to the comparator circuit 133.

In the case that the pattern having a dimension larger than the resolution of the optical system is provided in the sample 1 of the inspection target, the optical image data of the pattern is transmitted from the sensor data input circuit 13 to the comparator circuit 133. In the comparator circuit 133, the optical image data transmitted from the sensor data input circuit 13 and the reference image data generated by the reference circuit 132 are compared to each other using a proper comparison determination algorithm, and the point at which an error exceeds a predetermined value is determined to be the defect. A coordinate of the defect, the optical image data that serves as a basis for the defect determination, and the reference image data is stored in the magnetic disk device 109.

The defect determination can be made by the following two kinds of methods. One is a method for determining the point to be defect in the case that a difference is greater than a predetermined threshold dimension is recognized between the position of an outline in the reference image data and the position of an outline in the optical image data. The other is a method for determining the point to be defect in the case that a ratio of the pattern line width in the reference image data and the pattern line width in the optical image data is greater than a predetermined threshold. In the method, a ratio of the distance between the patterns in the reference image data and the distance between the patterns in the optical image data may be used as the target.

The defect determination can similarly be made for the repetitive pattern in which the period is less than or equal to the resolution of the optical system. For example, the variation of the average gradation value or the variation of the gradation value, which is obtained by the image processing circuit 108, may be transmitted to the comparator circuit 133 and compared to the gradation value in the reference image data by the comparator circuit 133. Alternatively, the average value of the pattern line widths or the irregularity data of the pattern edge may be transmitted from the image processing circuit 108 to the comparator circuit 133 and compared to the line width of the reference image data. As a result of the comparison, the determination that the optical image data has the defect can be made in the case that the difference between the optical image data and the reference image data is greater than the predetermined threshold.

For example, when the edge roughness increases partially in the repetitive pattern, when the pattern is partially lacked, or when the line width is partially narrowed, the disturbance is generated in the regularity to change the gradation value of the optical image data, which allows the defect to be detected. On the other hand, the gradation value of the optical image data fluctuates even if the edge roughness reaches the defect. Accordingly, the defective edge roughness and the non-defective edge roughness can be distinguished from each other by providing the predetermined threshold in the fluctuation of the gradation value.

The inspection apparatus and inspection method of the third embodiment are not limited to the die-to-database system, and a die-to-die system may be adopted. In this case, the reference image data becomes the optical image data different from the inspection target.

In the third embodiment, the focal position between the sample and the optical system is properly determined similarly to the first embodiment. Alternatively, the focal position may properly be determined similarly to the second embodiment. In this case, the light transmitted through the lens 11' in FIG. 10 is split by a mirror, and part of the light is incident to a focal position detecting image sensor (provided independently of the image sensor 12). The information is transmitted from the image sensor to the focal position detection circuit 14.

The inspection apparatus of the third embodiment may include a review function in addition to the inspection function. As used herein, a review means operation that is performed by an operator to determine whether the detected defect becomes troublesome from a practical standpoint.

For example, the coordinate of the point determined to be defective by the comparator circuit 133 in FIG. 10 and the optical image data and reference image data, which serve as the basis for the defect determination, are transmitted to a review device (not illustrated). The operator performs the review by comparing the reference image data that serves as the basis for the defect determination to the optical image data including the defect. Specifically, the image of the defective point in the sample 1 is displayed using the optical system (the light source 5, the lenses 6, 8, 9, and 11', the mirror 7, the image sensor 12, and the sensor data input circuit 13) in FIG. 10. At the same time, a criterion of the defect determination and the optical image data and reference image data, which serve as the basis for the defect determination, are displayed using a screen of the control computer 110 in FIG. 10. The defective information determined through the review is stored in the magnetic disk device 109 in FIG. 10.

When at least one defect to be corrected is checked through the review, the sample 1 is transmitted to a correction device (not illustrated) that is of an external device of the inspection apparatus 100 together with a defective information list. Because a correction method depends on a defective type, namely, a projected defect or a recessed defect, the kind of the defect including the distinction between the projection and the recess and the coordinate of the defect are added to the defective information list.

In the third embodiment, the line and space pattern is cited as an example of the repetitive pattern. However, the third embodiment is not limited to the line and space pattern. For example, the third embodiment may be applied to repetitive patterns such as the hole pattern.

For example, for the repetitive hole pattern in which the period is less than or equal to the resolution of the optical system is formed on the sample, when a shape defect exists due to the edge roughness or chip, the disturbance is generated in the regularity of the pattern, and the gradation value of the point where the shape defect exists exerts the value different from the surrounding gradation value. On the other hand, when the regular pattern is repeated with no shape defect, the gradation value of the optical image data becomes even. The change of the gradation value is also seen in the shape defects, which are caused by a hole diameter abnormality of the pattern and a gap abnormality with the adjacent pattern due to the position deviation of the pattern.

Accordingly, the inspection area of the sample is divided into predetermined unit regions to check the variation of the gradation value in each unit region, which allows the shape defect caused by the edge roughness or the lack of the pattern to be detected. For example, the predetermined unit region may be set to the area of 1 mm by 1 mm.

The shape defects, which are caused by the hole diameter abnormality of the pattern and the gap abnormality with the adjacent pattern due to the position deviation of the pattern, can also be detected by comparing the average gradation values of the unit regions to each other. When the diameters and gaps of the holes are even, the average gradation values of the unit regions becomes substantially equal. On the other hand, for example, when some hole diameters are reduced, there is a difference between the average gradation value of the unit region where the hole diameter abnormality is generated and the average gradation value of the unit region where the hole diameter is normal. When the position deviation of the pattern is generated to fluctuate the distance between the patterns, there is also a difference between the average gradation value of the unit region where the position deviation of the pattern is generated and the average gradation values of the other unit region.

In the case that the sample 1 including the hole pattern is inspected with the inspection apparatus 100 in FIG. 11, the optical image data of the pattern is transmitted from the sensor data input circuit 13 to the image processing circuit 108. In the image processing circuit 108, the pixel data in the optical image data is expressed by the gradation value in each pixel. Specifically, using the gray scale having 256 levels of the gradation values, one of the values of the 0 level to the 255 level is provided to each pixel. The inspection area of the sample 1 is divided into the predetermined unit regions to obtain at least one of either the average gradation value of each unit region or the variation of the gradation value in the unit region.

The information on the gradation value obtained by the image processing circuit 108 is transmitted to the defect detection circuit 134. The defect detection circuit 134 detects the defect of the sample 1 based on at least one of either the average gradation value or the variation of the gradation value.

The average gradation value is correlated with the average value of the pattern hole diameters. The variation of the gradation value in each unit region is correlated with the irregularity (the roughness) at the pattern edge. For example, the relational expression between the hole diameter and the gradation value is written by obtaining the value of the hole diameter measured with the length measuring SEM and the gradation value of the optical image data with respect to the predetermined pattern. The user can convert the average gradation value obtained by the image processing circuit 108 into the average value of the hole diameters in the defect detection circuit 134 using the relational expression. Even if the average gradation value is kept constant, it can be considered that the pattern edge has the large irregularity (the large roughness) in the case of the large variation of the gradation value in each unit region, namely, the large standard deviation of the gradation value.

The variation of the average gradation value or the variation of the gradation value, which is obtained by the image processing circuit 108, may be transmitted to the comparator circuit 133. In this case, the variation of the average gradation value or the variation of the gradation value is compared to the gradation value in the reference image data by the comparator circuit 133. Alternatively, the average value of the pattern hole diameters, into which the variation of the average gradation value or the variation of the gradation value is converted, or the irregularity data of the pattern edge may be transmitted from the image processing circuit 108 to the comparator circuit 133 and compared to the hole diameter of the reference image data, into which the variation of the average gradation value or the variation of the gradation value is converted. As a result of the comparison, the determination that the optical image data has the defect can be made in the case that the difference between the optical image data and the reference image data is greater than the predetermined threshold.

As described above, according to the inspection apparatus of the third embodiment, even if the repetitive pattern in which the period is less than or equal to the resolution of the optical system is formed on the sample, the optimum focal position between the sample and the optical system can be detected irrespective of the change in pressure or temperature by comparing the variations of the output values of optical image data to each other.

In the inspection apparatus of the third embodiment, the light source that emits the DUV (Deep Ultraviolet radiation) light can be used. Therefore, the inspection can be performed without the degradation of the throughput, which becomes troublesome in the case that the EB (Electron Beam) is used in the light source.

According to the inspection apparatus of the third embodiment, the area to be evaluated is divided into the predetermined unit regions to compare the average gradation values of the unit regions, which allows the abnormality of the line width or gap to be detected in the repetitive pattern in which the period is less than the resolution limit of the observation optical system. The irregularity of the pattern edge and the lack of the pattern can also be detected by checking the variation of the gradation value in each unit region.

The features and advantages of the present invention may be summarized as follows.

One aspect of the present invention provides the focal position detection apparatus that can detect the focal position of the sample having the repetitive pattern in which the period is less than or equal to the resolution of the optical system.

Another aspect of the present invention provides the inspection apparatus that can detect the defect in the repetitive pattern in which the period is less than or equal to the resolution of the optical system.

Still another aspect of the present invention provides the focal position detection method for being able to detect the focal position of the sample having the repetitive pattern in which the period is less than or equal to the resolution of the optical system.

Yet another aspect of the present invention provides the focal position detection method for being able to detect the defect in the repetitive pattern in which the period is less than or equal to the resolution of the optical system.

The present invention is not limited to the embodiments described and can be implemented in various ways without departing from the spirit of the invention.

The above description of the present embodiment has not specified apparatus constructions, control methods, etc. which are not essential to the description of the invention, since any suitable apparatus constructions, control methods, etc. can be employed to implement the invention. Further, the scope of this invention encompasses all focal position detection apparatuses, focal position detection methods, inspection apparatuses and inspection methods employing the elements of the invention and variations thereof which can be designed by those skilled in the art.

What is claimed is:

1. An inspection apparatus comprising:
   a light source that emits light having a predetermined wavelength;
   a first lens that transmits the light having the predetermined wavelength toward a sample;
   a second lens that forms an image of the light transmitted through or reflected by the sample via the first lens;
   an image sensor that obtains multiple optical image data of a pattern formed on the sample from the light of which the image is formed by the second lens, each optical image data in the multiple optical image data including a gradation value for each of a plurality of pixels;
   a focal position detector that determines, for each of the multiple optical image data, a variance or a standard deviation of the gradation values in the corresponding optical image data, detects a reference focal position of an image plane of the sample from the variance or the standard deviation of the gradation values in each of the multiple optical image data of the sample obtained by the image sensor, each of the multiple optical image data being acquired by changing a distance between the first lens and the sample, and detects an optimum focal position of an inspection from the reference focal position;
   an image processor that obtains at least one of either an average gradation value in each predetermined unit region or a variation of a gradation value in the unit region with respect to the optical image data obtained at the optimum focal position; and
   a defect detector that detects a defect of the sample based on at least one of either the average gradation value or the variation of the gradation value,
   wherein a resolution limit determined by a wavelength of the light source and a numerical aperture of the second lens is a value in which the pattern is not resolved.

2. The inspection apparatus according to claim 1, further comprising:
   a table on which the sample is placed; and
   a controller that adjusts a level of the table based on the optimum focal position detected by the focal position detector.

3. The inspection apparatus according to claim 2, wherein a support member that supports the sample is provided in the table, and
   the support member is disposed so as to support the sample at three points.

4. An inspection apparatus comprising:
   a light source that emits light having a predetermined wavelength;
   a first lens that transmits the light having the predetermined wavelength toward a sample;
   a second lens that forms an image of the light transmitted through or reflected by the sample via the first lens;
   a first image sensor that obtains optical image data of a pattern formed on the sample from the light of which the image is formed by the second lens;
   an optical path splitting unit that is disposed between the second lens and the first image sensor to split the light transmitted through the second lens;
   a second image sensor that obtains pieces of image information on focal points ahead and behind the pattern from the pieces of light split by the optical path splitting unit, each piece of image information in the pieces of image information including a gradation value for each of a plurality of pixels;
   a focal position detector that determines, for each of the pieces of image information on the focal points, a variance or a standard deviation of the gradation values in the corresponding piece of image information on the focal points, detects a reference focal position of an image plane of the sample in the first image sensor from the variance or the standard deviation of the gradation values in each of the pieces of image information on the focal points ahead and behind the pattern, each of the pieces of image information being acquired by changing a distance between the first lens and the sample, and detects an optimum focal position of an inspection from the reference focal position;
   an image processor that obtains at least one of either an average gradation value in each predetermined unit region or a variation of a gradation value in the unit region with respect to the optical image data obtained at the optimum focal position; and
   a defect detector that detects a defect of the sample based on at least one of either the average gradation value or the variation of the gradation value, wherein a resolution limit determined by a wavelength of the light source and a numerical aperture of the second lens is a value in which the pattern is not resolved.

5. The inspection apparatus according to claim 4, further comprising:
a table on which the sample is placed; and
a controller that adjusts a level of the table based on the optimum focal position detected by the focal position detector.

6. The inspection apparatus according to claim 5, wherein a support member that supports the sample is provided in the table, and
the support member is disposed so as to support the sample at three points.

7. An inspection method comprising the steps of:
irradiating a sample with light having a predetermined wavelength via a first lens, forming an image of the light transmitted through or reflected by the sample on an image sensor via a second lens, and obtaining multiple optical image data of a pattern by performing actions to obtain the multiple optical image data of the pattern formed in the sample with a distance between the first lens and the sample changed, each optical image data in the multiple optical image data including a gradation value for each of a plurality of pixels;
determining, for each of the multiple optical image data, a variance or a standard deviation of the gradation values in the corresponding optical image data;
detecting a reference focal position of an image plane of the sample from the variance or the standard deviation of the gradation values in each of the multiple optical image data, and detecting an optimum focal position of an inspection from the reference focal position;
adjusting a level of a table on which the sample is placed based on the optimum focal position;
obtaining at least one of either an average gradation value in each predetermined unit region or a variation of a gradation value in the unit region with respect to the optical image data obtained at the optimum focal position; and
detecting a defect of the sample based on at least one of either the average gradation value or the variation of the gradation value,
wherein the pattern is a repetitive pattern having a period less than or equal to resolution determined by the wavelength and a numerical aperture of the second lens.

8. The inspection method according to claim 7, wherein the sample is supported at three points by a support member provided in the table.

9. The inspection method according to claim 7, wherein the optimum focal position is a focal position that is deviated from the reference focal position by a predetermined offset amount.

* * * * *